United States Patent

Schall et al.

[11] Patent Number: 5,824,111
[45] Date of Patent: Oct. 20, 1998

[54] METHOD FOR FABRICATING A PROSTHETIC LIMB SOCKET

[75] Inventors: Scott R. Schall, Englewood; Tracy C. Slemker, Clayton, both of Ohio

[73] Assignee: Prosthetic Design, Inc., Clayton, Ohio

[21] Appl. No.: 791,934

[22] Filed: Jan. 31, 1997

[51] Int. Cl.$^6$ .................................. A61F 2/60; A61F 2/78
[52] U.S. Cl. ............................ 623/33; 623/27; 623/901; 264/40.1; 264/40.5
[58] Field of Search .................................. 623/33, 34, 27, 623/901; 264/40.1, 40.5

[56] References Cited

U.S. PATENT DOCUMENTS

| | | | |
|---|---|---|---|
| 5,152,800 | 10/1992 | Rothschild et al. | 623/33 |
| 5,252,822 | 10/1993 | Firth | 250/227.11 |
| 5,258,037 | 11/1993 | Caspers | 623/33 |
| 5,376,129 | 12/1994 | Faulkner et al. | 623/33 |
| 5,432,703 | 7/1995 | Clynch | 264/40.1 |
| 5,539,649 | 7/1996 | Walsh et al. | 364/474.05 |
| 5,662,715 | 9/1997 | Slemker | 623/33 |

FOREIGN PATENT DOCUMENTS 2069847  9/1981  United Kingdom.
2018186  8/1982  United Kingdom.

Primary Examiner—Paul B. Prebilic
Attorney, Agent, or Firm—Thompson Hine & Flory LLP

[57] ABSTRACT

A system and method for fabricating a thermoplastic prosthetic limb socket from a thermoplastic preform cone involves the steps of: obtaining a digital or physical positive representation of a patient's residual limb; determining a desired thickness for the thermoplastic socket; selecting a thermoplastic preform cone; calculating the dimensions of a proximate extension to be added to the proximate end of the digital or physical representation of the patient's residual limb based upon the dimensions of the patient's residual limb, the dimensions of the preform cone, and the desired thickness of the thermoplastic socket; forming a positive socket mold based upon the combined dimensions of the patient's residual limb and the extension; heating the preform cone; and stretching the preform cone over the positive cast. Preferably the method is performed on a CAD tool. The processing unit in the CAD tool has access to the dimensions of the residual limb, the desired thickness of the socket and the dimensions of the preform cone; and is thus able to compute the dimensions of the proximate extension based upon a set of algorithms stored in the form of a software package (or program) accessible and executable by the CAD's processing unit.

15 Claims, 7 Drawing Sheets

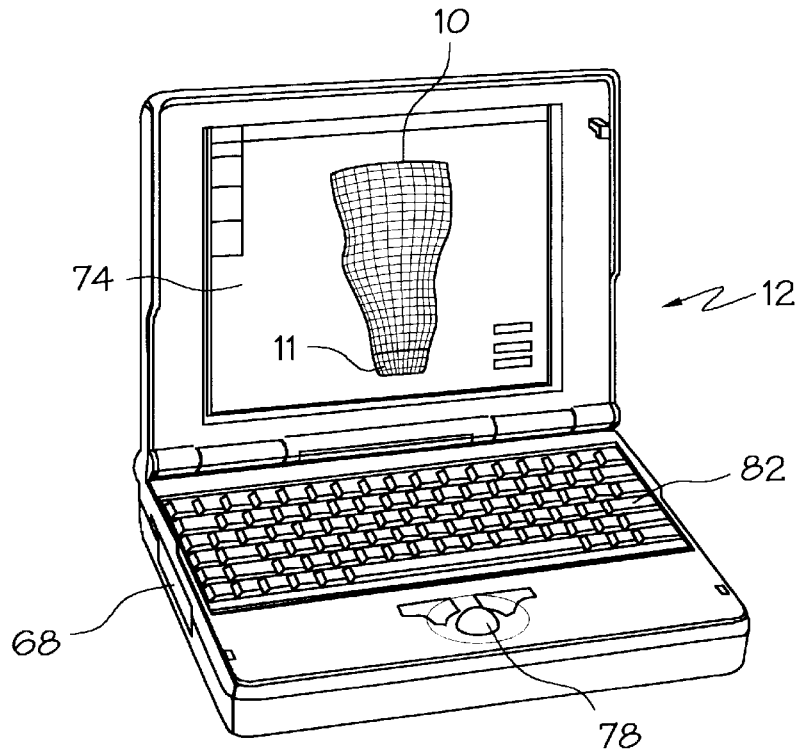
FIG. 1
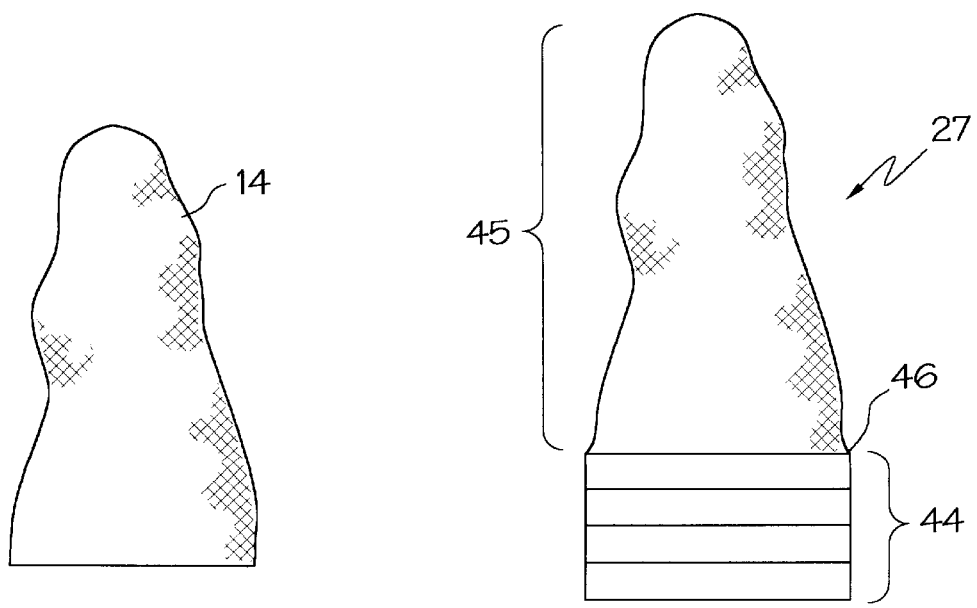
FIG. 2
FIG. 6

METHOD FOR FABRICATING A PROSTHETIC LIMB SOCKET

BACKGROUND

The present invention involves a system and method for fabricating a prosthetic limb socket, and more particularly to a system and method for insuring a wrinkle free thermoplastic prosthetic limb socket, having a consistent wall thickness, by determining the precise dimensions of an extended portion to be added to the proximate end of the positive cast (positive socket mold) for molding the prosthetic limb socket.

A prosthesis is often used to replace an amputated portion of a limb and to help restore the amputee's ability to use that limb. A prosthesis for a lower extremity amputation will often include an artificial foot connected to an upright assembly which is in turn connected to a custom fitted socket assembly. If the amputation is an above-the-knee ("AK"), the upright assembly will often commonly include an artificial knee joint.

The socket assemblies typically include an outer socket fabricated from a hard thermoplastic material. These outer sockets are typically created by heating a thermoplastic preform cone, stretching the heated cone over a positive cast of the amputee's residual limb and then vacuum forming the cone in place over the positive cast.

Presently there are several types and sizes of the thermoplastic preform cones. The types of material available for the preform cones include a clear thermoplastic material, a polypropylene polymer material, a polypropylene homopolymer material, and a flexible thermoplastic material. The available sizes for these preform cones typically range from a 16 cm base diameter to a 25 cm base diameter. The size of the preform cone to be selected typically is based upon measured geometrical dimensions of the positive cast of the residual limb.

To create the outer socket from the preform cone, the preform cone is then heated and stretched over the positive cast of the residual limb. These heating and stretching steps are commonly performed on a Socket Manufacturing Unit ("SMU"). A typical SMU will include a vertically translatable platform for mounting the preform cone thereto. The positive cast of the patient's residual limb will be placed onto a suction seat, which is in vertical alignment with and below the platform. The platform is first lifted such that the preform cone enters into a heating chamber at the top of the SMU, where it is heated for a sufficient amount of time to become soft and pliable. The heated preform cone is then lowered by the platform to stretch over the positive cast and suction seat. Next, the heated preform cone is sealed over the positive cast and the circumference of the suction seat, and a vacuum pump creates a vacuum between the heated preform cone and the modified positive cast, causing the preform cone to be intimately molded over the positive cast. Once the thermoplastic material has cooled and sufficiently solidified, the positive cast is extracted from the thermoplastic material and excess thermoplastic material is removed from the molded socket, leaving a finished thermoplastic socket component; and once this socket component has been fabricated, the remaining portions of the patient's prosthetic limb can be assembled.

To attain a desired thickness of the finished socket, the preform cone must typically be stretched a certain distance beyond the proximate (or proximal) end of the positive cast (i.e., the thickness of the socket will be linearly dependent upon the amount that the preform cone has been stretched along or beyond the positive cast); and typically, the fabricator must estimate the amount that the preform cone must be stretched beyond the positive cast of the residual limb to attain the desired thickness. To extend the length of the positive cast, and in turn, to control the thickness of the finished socket, the fabricator will typically attach or stack objects (such as wooden blocks) to the proximate end of the positive cast, thus lengthening the positive mold.

As discussed above, the size of the object to attach to the proximate end of the positive cast is estimated by the fabricator based primarily upon the fabricator's experience with the process. A disadvantage with this estimation is that it is very difficult to obtain a desirable thickness of the prosthetic limb socket, often requiring the fabrication process to be repeated.

Another problem with the present socket manufacturing processes is that the preform cone has a mouth at its proximate end with a circumference which is typically significantly larger than the circumference of the positive cast (or proximate built-up portions) at the proximate end of the positive cast (or proximate built-up portions). Accordingly, when the preform cone is heated and suction fit over the positive cast and any proximate built-up portions, the extra plastic material of the preform cone material at the proximate end of the positive cast will sometimes wrinkle and form creases along the built-up portions. These creases and wrinkles will many times extend all the way up to the portion of the finished socket which covers the positive cast of the residual limb. This portion of the finished socket is often the portion to remain after the waste portions have been discarded; and thus, creases or wrinkles extending into this often cause fracture points or cause 'pinching' or other discomfort to the wearer. Accordingly, creases or wrinkles extending into this 'remaining' portion of the socket, for all intents and purposes, ruins the socket, requiring the socket to be refabricated.

Accordingly a need exists for a system and method which will allow the prosthetic limb socket fabricators to consistently control the thickness of the prosthetic limb sockets which are created by molding a preform cone over a positive cast of the patient's residual limb. There is also a need for a way to substantially eliminate the formation of creases and wrinkles in the finished version of the thermoplastic socket.

SUMMARY

The present invention provides a system and method for fabricating a thermoplastic prosthetic limb socket from a thermoplastic preform cone, and in particular, provides a method for calculating an extended portion to be added to a proximate end of a positive socket mold. The method of the present invention involves the steps of: (a) obtaining a digital or physical positive representation of a patient's residual limb; (b) determining a desired thickness for the thermoplastic socket; (c) selecting a thermoplastic preform cone; (d) calculating the dimensions of a proximate extension to be added to the proximate end of the digital or physical representation of the patient's residual limb based upon the dimensions of the patient's residual limb, the dimensions of the preform cone, and the desired thickness of the thermoplastic socket; (e) forming a positive socket mold based upon the combined dimensions of the patient's residual limb and the extension; (f) heating the preform cone; and (g) stretching the preform cone over the positive cast.

Preferably the calculating step includes the steps of: computing a first volume of the preform cone, which is to be molded over the positive representation of the patient's residual limb with the desired thickness; subtracting this first volume from an initial volume of the preform cone to obtain a remaining volume of the preform cone; and computing the dimensions of the socket extension sufficient to have this remaining portion of the preform cone molded over a circumferential surface thereof with the desired thickness.

Preferably the above method is performed on a computer-aided-design tool (CAD) which includes memory for storing the dimensions of the patient's residual limb, and includes a memory for storing the dimensions of the extension to be added to the dimensions of the patient's residual limb. The CAD tool may have a way for a user to input or download a desired thickness for the finished socket, or may have a predetermined thickness designated. The CAD tool may contain the dimensions for all available preform cones, including the selected preform cone, or the CAD tool may have a way to facilitate the entry or download of the relevant dimensions of the preform cone. The processing unit in the CAD tool has access to the dimensions of the residual limb, the desired thickness of the socket and the dimensions of the preform cone; and is thus able to compute the dimensions of the proximate extension based upon a set of algorithms stored in the form of a software package (or program) accessible and executable by the CAD's processing unit.

Once the dimensions for the extension have been added to the proximate end of the dimensions of the patient's residual limb, the combined dimensions are then preferably downloaded to a computer-numerically-controlled (CNC) milling machine, which mills the positive socket mold from a suitable carving blank, based upon the combined dimensions of the residual limb and the calculated extension.

Once this positive socket mold has been milled by the CNC milling machine, it and the preform cone are placed into the SMU, which heats the preform cone, stretches the preform cone over the positive socket mold and suction fits the heated preform cone to the positive socket mold.

Preferably, the mold extension is designed to have an outwardly flared proximate circumference, such that when the preform cone is suction fit to the positive socket mold, the flared end of the mold extension helps to conform to the large proximate end of the preform cone, thus helping to substantially eliminate the formation of creases and wrinkles in the finished product.

Accordingly, it is an object of the present invention to facilitate the creation of an extension to a positive socket mold, for molding a thermoplastic preform cone thereover, to produce a prosthetic limb socket having a consistent and even wall thickness; it is an object of the present invention to facilitate the use of a CAD tool to calculate the dimensions of the mold extension and to download the combined dimensions of the residual limb and cast extension to a CNC milling machine so that the entire positive socket mold can be produced; and it is an object of the present invention to provide a mold extension which substantially eliminates the formation of creases or wrinkles when the preform cone is molded thereover. These and other objects and advantages of the present invention will be apparent from the following description, the accompanying drawings and the appended claims.

BRIEF DESCRIPTION OF THE DRAWINGS

FIG. 1 is a perspective view of a CAD tool for use with the present invention;

FIG. 2 is a perspective side view of a positive cast of a patient's residual limb;

FIG. 6 is a perspective side view of a positive mold including a proximate extension for fabricating a prosthetic limb socket;

DETAILED DESCRIPTION

Figure 3:
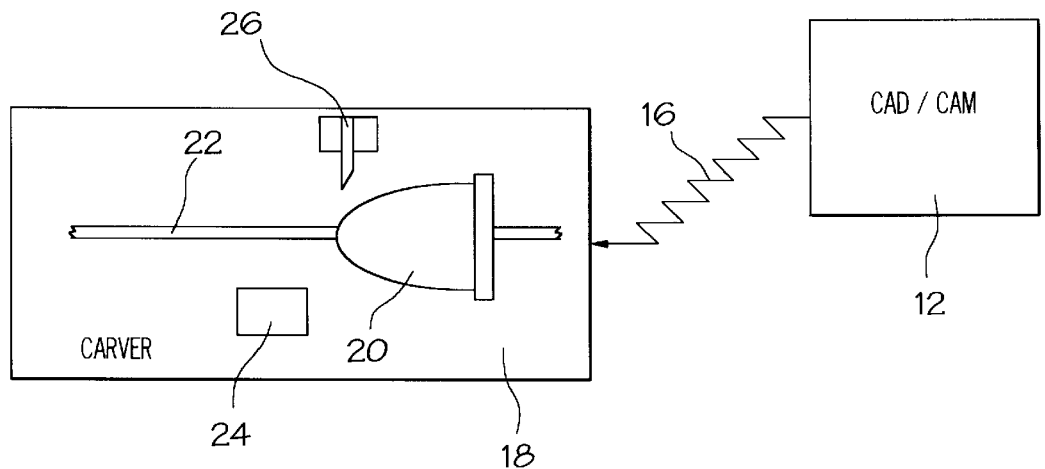
FIG. 3 is a schematic block diagram representation of the CAD tool and CNC milling machine for use with the present invention.

As shown in FIGS. 1 and 2, a positive representation of a patient's residual limb can be in the form of a digital representation 10 as stored in a computerized design tool, depicted in FIG. 1 as a laptop CAD system 12 or can be a physical positive cast 14 of the patient's residual limb formed by any conventional method as presently known in the art. For example, the positive cast 14 can be formed by the process of: applying a plaster bandage onto the patient's residual limb, and molding it as it dries; removing the negative cast from the patient's residual limb and filling the negative cast with plaster; and when the plaster is dry, the negative cast is cut off, producing the positive cast 14 of the patient's residual limb. This positive cast 14 may then be modified with a file to remove plaster in the "soft areas" of the residual limb and, may also be modified by adding plaster in the "sensitive areas" of the residual limb. Such modifications, are performed according to the arrangement and positions of the skeletal areas and soft tissue areas of the patient's residual limb, such that when the prosthetic limb is created using this modified positive cast 14, the residual limb does not bear weight on the distal end of the limb but rather on the areas around the residual limb.

There are also several known methods for obtaining the digital representation of the patient's residual limb 10 as depicted in FIG. 1. For example, such methods include the use of wand-based CAD systems such as the TracerCAD system, commercially available from Tracer Corporation of Miami, Fla., or by a digitizing system such as the Benz CAD/CAM and Digitizing systems, available through Benz Group Limited, Horns Cross, Greenhithe, Kent U.K. Such CAD systems are also capable of making the modifications to the digital representation of the limb, similar to the manual modifications described above, based upon the skeletal and muscular positions in the patient's limb such that a finished prosthetic limb does not bear upon the distal end of the residual limb but rather on the areas around the residual limb. Such CAD systems can also add dimensions of interconnection components 11, which must be inserted into the interior of the finished socket during assembly of the prosthetic limb, to the dimensions of the digital representation 10. An example of such an interconnection component is a Socket Seal attachment plate system commercially available through Prosthetic Design Inc., Clayton, Ohio.

As shown in FIG. 3, if a CAD tool 12 is used to store and modify the digital representation 10 of the patient's residual limb, the CAD tool 12 will preferably transmit the dimensions of the modified digital representation, via a data link 16, to a computer-numerically-controlled ("CNC") milling machine 18. An appropriate CNC milling machine for use with the present invention is a "Benz Carver l" available from Benz Group Limited, Horns Cross, Greenhithe, Kent, U.K. Upon receiving the dimensions of the modified digital representation of the patient's residual limb, the CNC milling machine 18 will use the dimensions to carve a positive socket mold from a carving blank 20. The carving blank 20 is fixed to a rotating shaft 22, and the internal control system 24 of the milling machine controls the radial and axial movement of a carving tool 26 with respect to the carving blank 20. The carving blank 20 can be a plaster, urethane foam or other type of material suitable for the uses described herein. Suitable carving blanks for use with the present invention are commercially available through Prosthetic Design, Inc., Clayton, Ohio.

Figure 4:
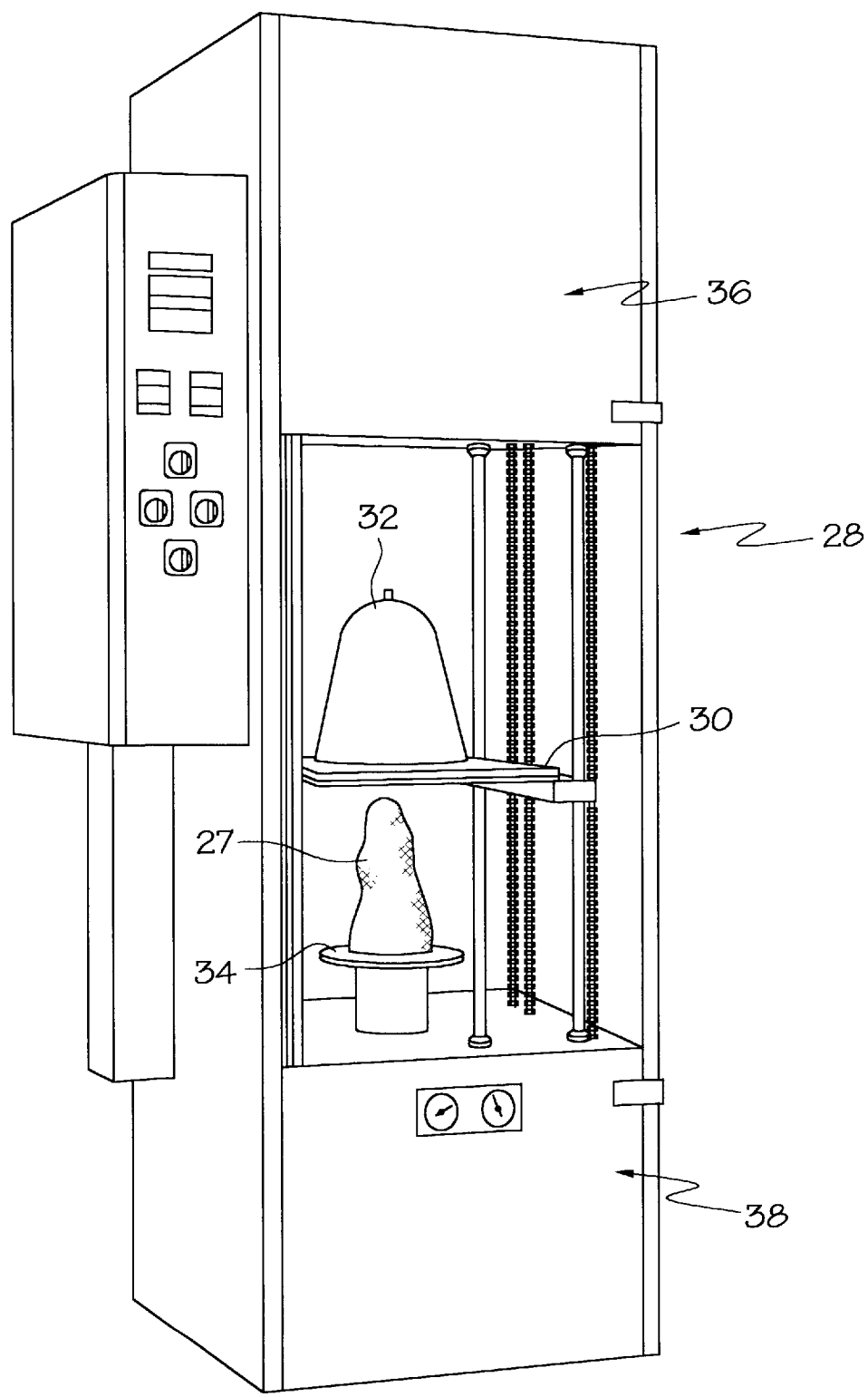
FIG. 4 is a perspective view of a socket manufacturing unit for use with the present invention.

As shown in FIG. 4, once the positive socket mold 27 has been created, either by hand or by the automated milling operations discussed above, the positive mold 27 is taken to a socket manufacturing unit ("SMU") 28 for forming a thermoplastic socket thereabout. A suitable SMU for use with the present invention is commercially available through Prosthetic Design, Inc., Clayton, Ohio. A typical SMU 28 will include a vertically translatable platform 30 for mounting a thermoplastic preform cone 32 thereto.

Figure 9:
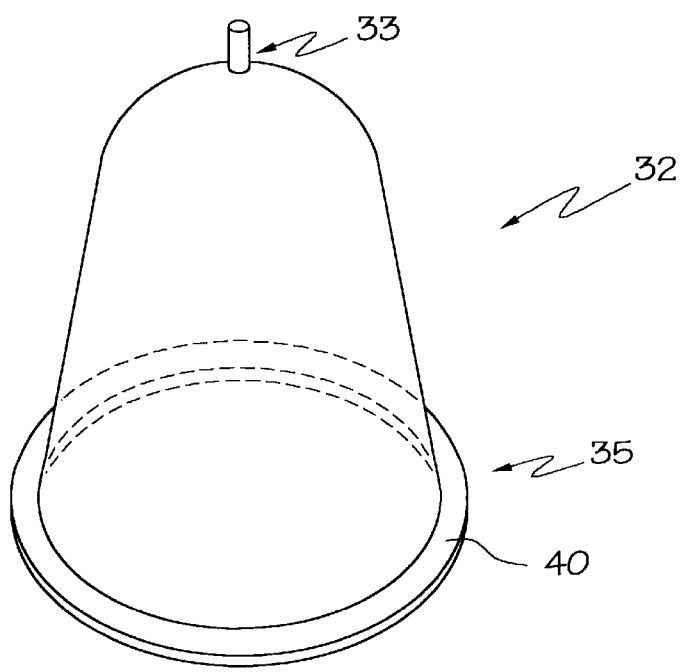
FIG. 9 is a perspective view of a preform cone.

As shown in FIG. 9, a typical preform cone 32 is a hollow cone with a rounded distal end 33 and an open proximate end 35. The circumference of the preform cone increases with the distance from the distal end 33. A flange 40 extends radially outward from the proximate end 35 and facilitates mounting to the translatable platform 30 of the SMU. Such preform cones 32 are typically formed from a clear thermoplastic material, a polypropylene polymer material, a polypropylene homopolymer material, or a flexible thermoplastic material; are available in sizes that will typically range from 16 cm base diameter to 25 cm base diameter; and are commercially available through Prosthetic Design, Inc., Clayton, Ohio.

Figure 13:
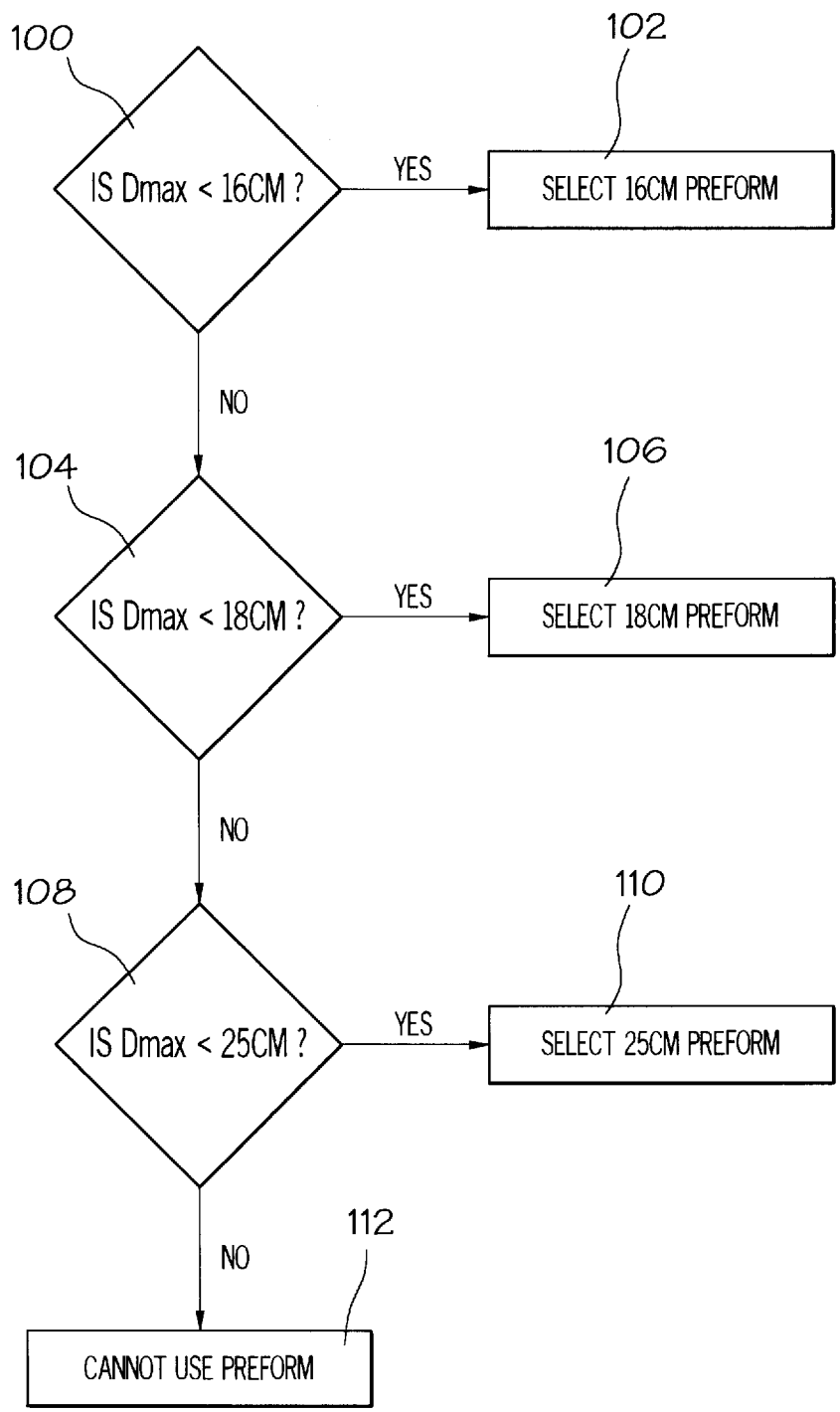
FIG. 13 is a flow-chart illustrating a method of the present invention for selecting a preform cone.

The preform cones are presently commercially available in the United States in three sizes: 16 cm, 18 cm and 25 cm. As shown in FIG. 13, a method for determining the size of the preform cone to use is based upon the maximum diameter (Dmax) that the positive mold 27 will have. In block 100, if Dmax is less than 16 cm, select the 16 cm preform cone in block 102; if not less than 16 cm, advance to block 104. In block 104, if Dmax is less than 18 cm, select the 18 cm preform cone in block 106; if not less than 18 cm, advance to block 108. In block 108, if Dmax is less than 25 cm, select the 25 cm preform cone in block 110; if not less than 25 cm, advance to block 112, indicating that a preform cone cannot be used and some other method of fabricating the socket must be utilized.

Referring again to FIG. 4, the positive mold 27 will be mounted to a suction seat 34, which is positioned below the platform such that the positive mold is in vertical alignment with the preform cone 32. The platform 30 is lifted such that the preform cone 32 enters into a heating chamber 36 at the top of the SMU, and is heated for a sufficient amount of time for the preform cone to become soft and pliable. Once sufficiently soft and pliable, the heated preform cone 32 is lowered by the platform 30 unit the heated preform cone stretches over the positive mold 27 and suction seat 34. Next, a seal is formed between the heated preform cone 32, the positive mold 27, and the suction seat 34, and a vacuum pump positioned within the vacuum chamber 38 creates a vacuum between the heated preform cone 32, the positive mold 27, and the suction seat 34, and in turn, causes the preform cone 32 to conform to the positive mold 27. Once the material of the preform cone 32 has cooled and sufficiently solidified, the positive mold is extracted from the solidified material, any excess material is removed, and the proximate surfaces of the molded preform cone are then smoothed leaving a finished socket component. Once this socket component has been fabricated, the remaining portions of the patient's prosthetic limb can be assembled thereto.

Figure 5:
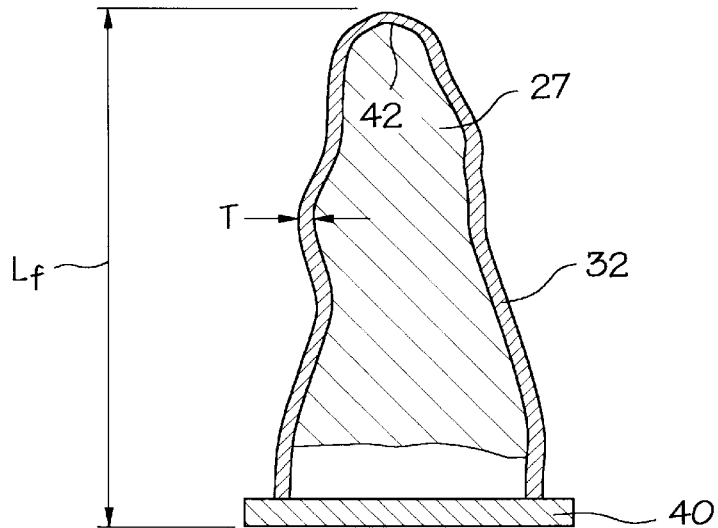
FIG. 5 is a cross-sectional side view of a preform cone molded over a positive mold.

As shown in FIG. 5, when the preform cone 32 has been suction fit to the positive mold 27, the thickness of the finished socket T will depend upon the distance $L_f$ that the flange 40 of the preform cone 32 has been stretched below a distal end 42 of the positive mold 27. For example, as $L_f$ increases, the thickness T of the preform cone 32 (and in turn, the finished socket) will linearly decrease.

Figure 7:
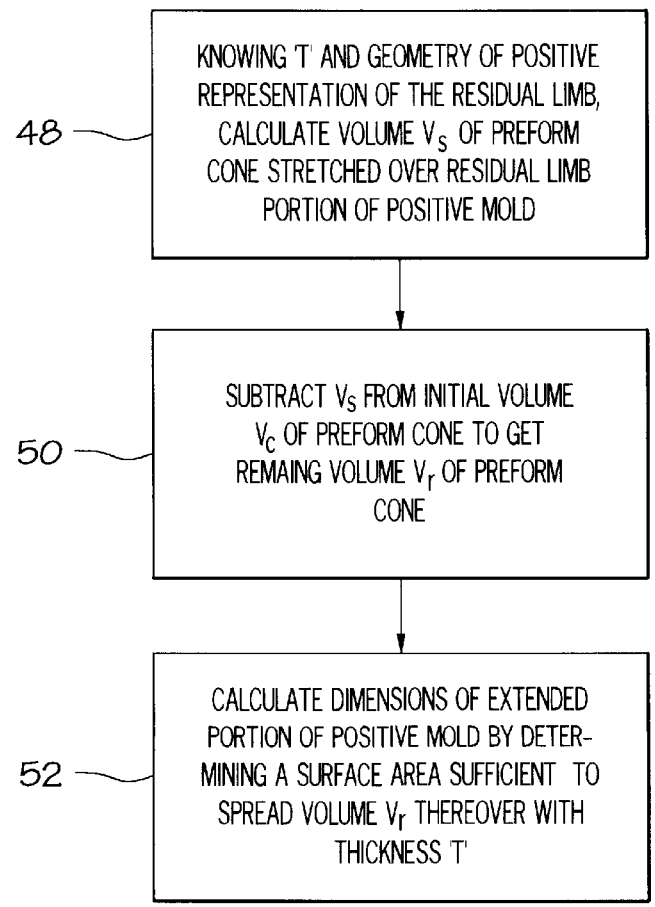
FIG. 7 is a flow-chart illustrating a method of the present invention for calculating an extended portion of the socket mold.
Figure 8:
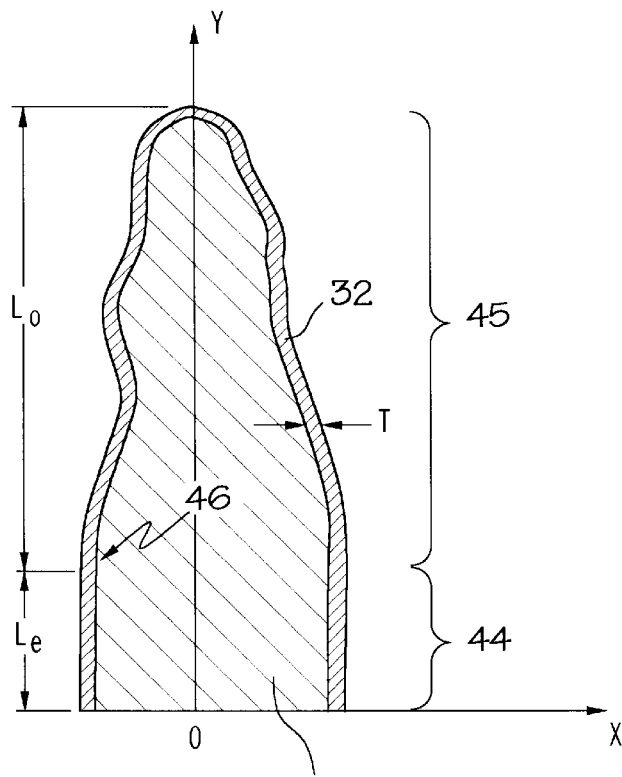
FIG. 8 is a cross-sectional side view of a preform cone molded over a positive mold having an extended portion, the dimensions of which were calculated according to the present invention.

As shown in FIG. 6 and 8, knowing the desired thickness T of the finished socket, and certain geometrical dimensions of the modified positive cast (10 or 14) of the patient's residual limb, the CAD system 12 is able to calculate the dimensions of an extended portion 44 to be added to a proximate end 46 of a residual limb portion 45 of the positive mold 27. The general steps for calculating the dimensions of the extended portion 44 of the positive mold 27 is as shown in FIG. 7: In step 48, a volume $V_s$ of the preform cone, having the desired thickness T, stretched over the residual limb portion 45 of the positive mold 27 is calculated; in step 50, the remaining volume $V_r$ of the preform cone is determined by subtracting the volume $V_s$ from the initial volume $V_c$ of the preform cone (the initial volume $V_c$ does not include the volume of the flange 40); and in step 52, the dimensions of the extended portion 44 of the positive mold 27 are calculated by determining a surface area sufficient to for this remaining volume $V_r$ to spread thereover with the desired thickness T.

Referring to FIG. 8, an example set of calculations for determining the dimensions of the extended portion 44 of a positive representation of a patient's residual limb are as follows:

Knowing the diameter $D_y$, and the circumference $C_y$ of the residual limb portion 45, at any vertical point along a Y axis (from the dimensions of the modified positive cast 10, 14) and knowing the length $L_o$ of the residual limb portion 45, a volume $V_s$ of the preform cone, having the desired thickness T, stretched over the residual limb portion 45 of the positive mold 27 is calculated as follows (note that because the residual limb portion is never perfectly round, the diameter $D_y$ can be an average diameter at a vertical point and the circumference $C_y$ can be the length around a perimeter of the residual limb portion at a vertical point, etc.):

First, the circumferential area $A_y$ of the molded cone at any vertical point 'Y' is determined.

$$A_y = \eta(2TD_y)^2 - \eta D_y^2 \quad \text{(Eq. 1)}$$

$$A_y = \eta 4T^2 D_y^2 - \eta D_y^2 \quad \text{(Eq. 2)}$$

let $D_y = C_y/\eta$, then  (Eq. 3)

$$A_y = 4T^2 C_y^2/\eta - C_y^2/\eta \quad \text{(Eq. 4)}$$

Thus, knowing the circumferential area $A_y$ of the molded cone at any vertical point, the volume $V_s$ of the preform cone molded over the residual limb portion of the mold is calculated as:

$$V_s = \int_\phi^{L_o} (4T^2 C_y^2/\pi) y \, dy - \int_\phi^{L_o} (C_y^2/\pi) y \, dy \quad \text{(Eq. 5)}$$

Knowing the initial volume $V_c$ of the preform cone 32, the remaining volume $V_r$ of the preform cone is determined by subtracting the volume $V_s$ from the initial volume $V_c$ (the initial volume $V_c$ does not include the volume of the flange 40) as follows:

$$V_r = V_c - V_s \quad \text{(Eq. 6)}$$

Finally, upon selecting a desired circumference $C_e$ of the extended portion 44, the length $L_e$ of the extended portion 44 can be calculated as follows (again, because the residual limb portion is never perfectly round, the extended portion should also not be perfectly round, and thus the circumference $C_e$ can be the length around a perimeter of the extended portion at a vertical point, for example):

$$L_e = \frac{V_r}{4T^2 C_e^2/\pi - C_e^2/\pi} \quad \text{(Eq. 7)}$$

Accordingly, the dimensions $L_e$ and $C_e$ can be used to fabricate the extended portion 44 of the positive mold 27.

Figure 10:
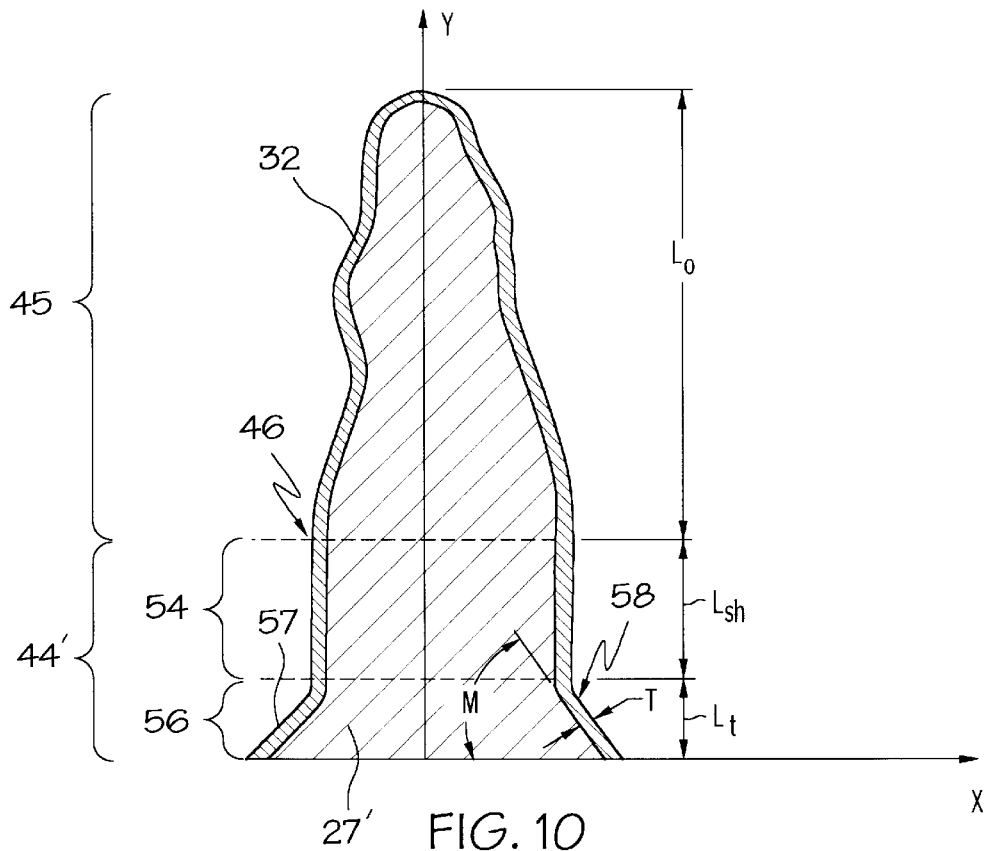
FIG. 10 is a cross-sectional side view of a preform cone molded over a positive mold having an extended portion, the dimension of which were calculated according to an alternate embodiment of the present invention.

In a preferred embodiment of the positive mold 27', as shown in FIG. 10, the extended portion 44' is broken up into a shank portion 54 and a flared portion 56. The flared portion 56 is positioned at the proximate end 58 of the extended portion and flares radially outwardly and downwardly (in the proximate direction). This flared portion 56 helps conform to the large diameter open proximate end 35 of the preform cone 32; and accordingly, when the preform cone 32 is molded over the positive cast, the flared portion 56 helps to reduce the formation of creases and wrinkles in the finished product.

Preferably the outer surface 57 of the flared portion 56 is angled upward from the X coordinate axis at an angle M, which ranges from 70° to 85° (and correspondingly, the flared portion 56 flares outwardly with respect to the vertical axis at an angle preferably ranging from 15° to 20°); and in the preferred embodiment, ranges from 76° to 80°. From the angle M, a slope m of the outer surface 57 of the flared portion 56 is easily determined. Knowing the slope m, the initial height b of the preform cone 32, and the circumference $C_m$ of the residual limb portion 45 at its proximate end 46, the length $L_t$ of the flared portion 56 is calculated as follows:

$$L_t = m(C_m/2\eta) + b \quad \text{(Eq. 8)}$$

Figure 11:
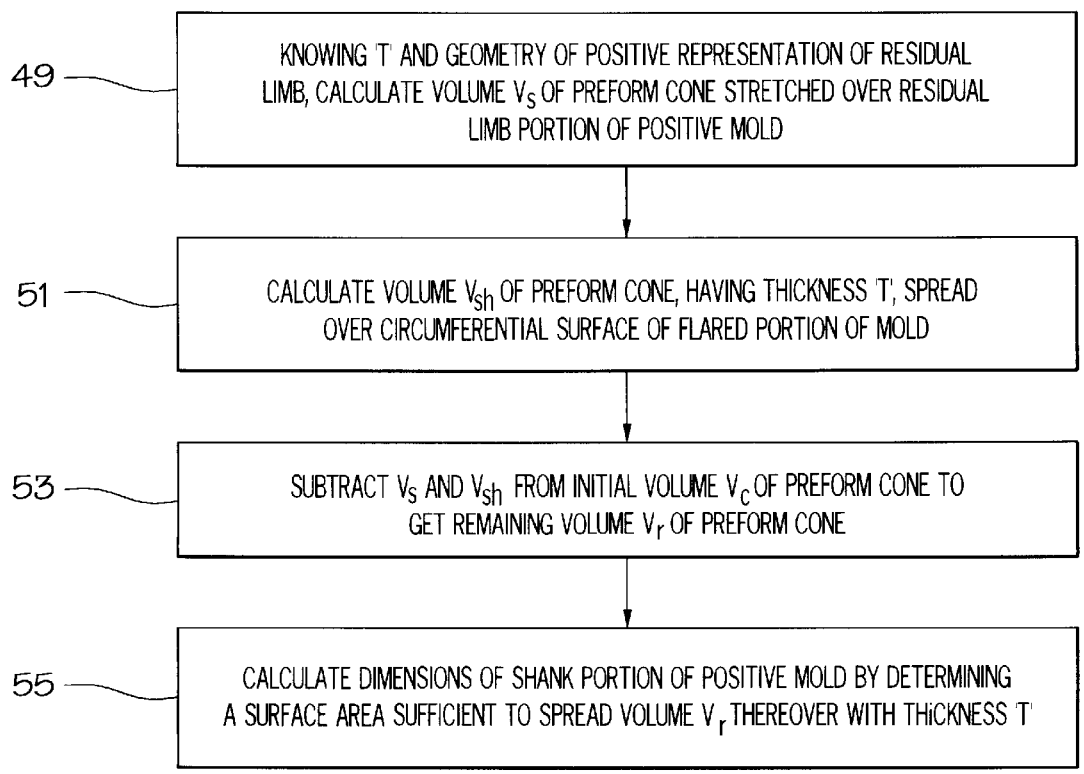
FIG. 11 is a flow-chart illustrating a method of an alternate embodiment of the present invention for calculating an extended portion of the socket mold have an outwardly flared proximate end.

General steps for calculating the dimensions of the extended portion 44' of the positive mold 27', having the shank portion 54 and flared portion 56, as shown in FIG. 11 are: In step 49, a volume $V_s$ of the preform cone, having the desired thickness T, stretched over the residual limb portion 45 of the positive mold 27' is calculated; in step 51, a volume $V_f$ of the preform cone, having the desired thickness T, spread over the circumferential surface of the flared portion 56 is calculated; in step 53, the remaining volume $V_r$ of the preform cone is determined by subtracting the volumes $V_s$ and $V_f$ from the initial volume $V_c$ of the preform cone (the initial volume $V_c$ does not include the volume of the flange 40); and in step 55, the dimensions of the shank portion 54 of the positive mold 27' are calculated by determining a surface area sufficient for this remaining volume $V_r$ to be spread thereover with the desired thickness T.

Referring to FIG. 10, an example set of calculations for determining the dimensions of the extended portion 44' of a positive representation of a patient's residual limb are as follows:

Knowing the diameter $D_y$, and the circumference $C_y$ of the residual limb portion 45, at any vertical point along a Y axis (from the dimensions of the modified positive cast 10, 14) and knowing the length $L_o$ of the residual limb portion 45, a volume $V_s$ of the preform cone, having the desired thickness T, stretched over the residual limb portion 45 of the positive mold 27 is calculated as shown in Eqs. 1 through 5 above. Knowing the length $L_t$ of the flared portion 56 and knowing the diameter $D_y'$ and the circumference $C_y'$ of the flared portion 56, at any vertical point along a Y axis, a volume $V_f$ of the preform cone, having the desired thickness T, stretched over the circumferential surface of the shank portion 56 of the positive mold 27 is calculated as follows:

$$V_f = \int_\phi^{L_f} (4T^2 C_y'^2/\pi) y \, dy - \int_\phi^{L_t} (C_y'^2/\pi) y \, dy \quad \text{(Eq. 9)}$$

Knowing the initial volume $V_c$ of the preform cone 32, the remaining volume $V_r'$ of the preform cone is determined by subtracting the volumes $V_s$ and $V_f$ from the initial volume $V_c$ (the initial volume $V_c$ does not include the volume of the flange 40) as follows:

$$V_r' = V_c - (V_s - V_f) \quad \text{(Eq. 10)}$$

Finally, upon selecting a desired circumference $C_{sh}$ of the shank portion 54 (which is preferably the circumference $C_m$ of the residual limb portion 45 at its proximate end 46), the length $L_{sh}$ of the shank portion 54 can be calculated as follows:

$$L_{sh} = \frac{V_r'}{(4T^2 C_{sh}^2/\pi - C_{sh}^2/\pi)} \quad \text{(Eq. 11)}$$

Accordingly, the dimensions $L_t$, m, b, $L_{sh}$ and $C_{sh}$ can be used to fabricate the extended portion 44' of the positive mold 27'.

Figure 12:
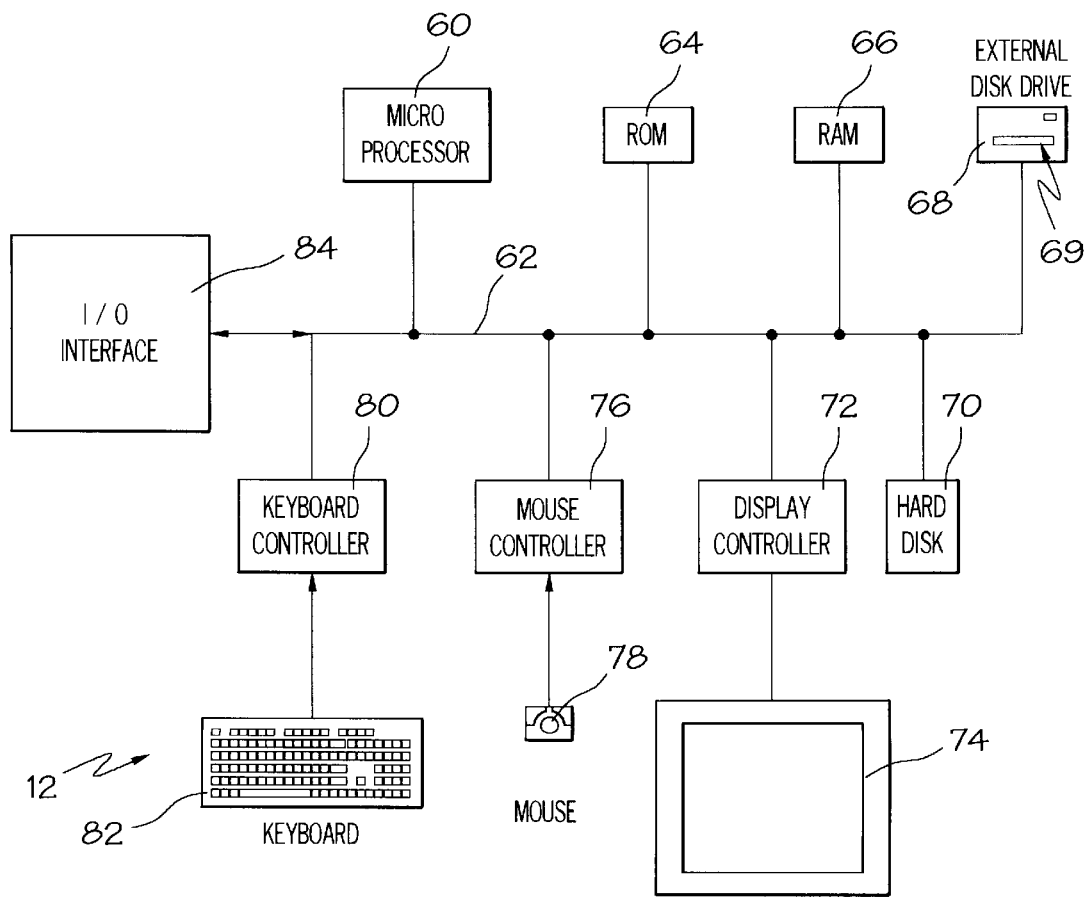
FIG. 12 is a schematic block diagram for the CAD tool of the present invention.

Preferably, as shown in FIGS. 1 and 12, the above calculations for determining the dimensions of the extended portions 44 or 44' (and also the selection of the desired preform cone size) are performed by the CAD system 12. A CAD system for use with the present invention can include a microprocessor 60 communicating over a communications bus 62 with an internal read-only memory ("ROM") 64, an internal random-access memory ("RAM") 66, at least one external disk drive 68 (adapted to read and/or write to external memory devices 69 such as floppy disks, CDs, etc.), a hard disk 70, a display controller 72 for operating a display 74, a mouse-controller 76 for interfacing a mouse device (a cursor control device such as a mouse, trackball, etc.) 78, a keyboard controller 80 for interfacing a keyboard 82 and at lease an Input/Output interface (such as a modem device, a network device, a serial port, etc.) 84.

To perform the above calculations, a program, such as a software program, configured to perform these calculations is stored either in the ROM 64, the RAM 66, the external memory device 69, the hard disk 70 or is accessible by the microprocessor 60 via an IO interface 84. When the microprocessor 60 is executing the program, the microprocessor 60 must have access to the dimensions of the positive representation of the patient's residual limb, which can be the digital representation 10 stored in any of the above memory devices, accessible through an IO interface 84, or can be typed in by the operator over the keyboard 82. Likewise, the microprocessor 60 must have access to the desired thickness T of the finished socket, the dimensions of the preform cone 32. These parameters can also be stored in any of the memory devices, accessible over the IO interface 84 or can be typed in by the operator using the keyboard 82. Once the dimensions of the extended portion 44 have been calculated, the microprocessor then preferably combines these dimensions with the dimensions of the digital representation 10 of the patient's residual limb, and then downloads these combined dimensions over the data link 16 to the milling machine 18 such that the milling machine 18 can mill the positive socket mold 27 or 27' (See FIG. 3). This socket mold 27 or 27' is then placed on the suction seat 34 of the SMU 28, and the preform cone 32 is then molded over this mold as discussed above (See FIG. 4). It should be apparent to one of ordinary skill in the art, that it is within the scope of the invention to perform some of the above steps manually or semi-manually (for example, downloading dimensions from the CAD tool to the milling machine by copying the dimensions to a floppy disk and inserting the floppy disk into a disk-drive incorporated into the milling machine).

Therefore, having described the invention in detail and by reference to the drawings, it will be apparent that modification and variations are possible without departing from the scope of the invention as defined in the following claims.

What is claimed is:

1. A method for fabricating a thermoplastic prosthetic limb socket comprising the steps of;

obtaining a representation of a patient's residual limb, the representation of the patient's residual limb having dimensions and a proximate end;

determining a desired thickness of the thermoplastic socket;

selecting a thermoplastic preform cone having dimensions;

computing a first volume of a portion of the preform cone, which is to be molded over the representation of the patient's residual limb and has the desired thickness, based upon the dimensions of the representation of the patient's residual limb and the desired thickness of the thermoplastic socket;

subtracting the first volume from an initial volume of the preform cone, to produce a remaining volume of the preform cone;

calculating dimensions of an extension, which is to be added to the proximate end of the representation of the patient's residual limb, the calculated dimensions being sufficient to mold a remaining portion of the preform cone with the desired thickness;

forming a positive mold based upon a combination of the dimensions of the extension and the dimensions of the representation of the patient's residual limb;

heating the preform cone; and stretching the heated preform cone over the positive mold.

2. The method of claim 1, wherein the representation of the patient's residual limb includes a proximate circumference, and the calculating step includes a step of designating a circumference of the extension to be substantially equal to or greater than the proximate circumference of the representation of the patient's residual limb.

3. The method of claim 2, wherein:

the extension has a distal end and a proximate end;

the designating step designates a circumference at the distal end of the extension and a circumference at the proximate end of the extension; and the circumference at the proximate end of the extension is larger than the circumference at the distal end of the extension.

4. The method of claim 3, wherein the designating step designates a circumference of the extension that gradually increases with the distance from the distal end of the extension.

5. The method of claim 1, wherein the dimensions of the representation of the patient's residual limb include a maximum diameter, and the selecting step includes the step of comparing the maximum diameter with diameters of various preform cone sizes.

6. The method of claim 1, wherein the representation of the patient's residual limb is a digital representation accessible by a computer-aided-design tool.

7. The method of claim 6, wherein the digital representation is modified using the computer-aided-design tool according to a skeletal or soft-tissue position.

8. The method of claim 6, wherein the computing, subtracting and calculating steps are performed by the computer-aided-design tool.

9. The method of claim 8, wherein said calculating step includes the step of creating a digital representation of the positive mold based upon a combination of the dimensions of the extension and the dimensions of the representation of the patient's residual limb.

10. The method of claim 8, wherein the forming step includes the steps of:

downloading the dimensions of the positive mold to a computer-numerically-controlled milling machine;

operating the milling machine to mill the positive mold.

11. The method of claim 10, further comprising a step of, after the stretching step, creating a vacuum between the preform cone and the positive mold.

12. The method of claim 11, wherein the heating, stretching and vacuum creating steps are performed by a socket manufacturing unit.

13. The method of claim 1, wherein the calculating step further includes the step of:

determining a circumference of the extension according to the dimensions of the representation of the patient's residual limb.

14. The method of claim 13, wherein the proximate end of the representation of the patient's residual limb has a circumference, and the calculating step further includes the steps of:

determining a circumference of the extension to be substantially equal to or greater than the circumference of the proximate end of the representation of the patient's residual limb; and computing a length of the extension from the remaining volume of the preform cone sufficient to cause a remaining portion of the preform cone, molded substantially over an entire circumferential surface of the extension, to have the desired thickness.

15. The method of claim 1, wherein the proximate end of the representation of the patient's residual limb has a circumference, wherein the method further comprises the steps of:

computing dimensions of a substantially frustoconically shaped proximate taper to the extension, the proximate taper having a circumferential surface, a distal circumference substantially equal to the circumference of the proximate end of the representation of the patient's residual limb, and a proximate circumference substantially larger than the distal circumference of the proximate taper; and computing a second volume of a portion of the preform cone, having the desired thickness, molded over the circumferential surface of the proximate taper;

wherein the subtracting step includes the step of subtracting the second volume from the initial volume of the preform cone; and wherein the computer step includes the step of computing a length of a shank portion of the extension from the remaining volume of the preform cone sufficient to cause the remaining portion of the preform cone, molded substantially over an entire circumferential surface of the shank portion of the extension, to have the desired thickness.

* * * * *